US00PP09751P

United States Patent [19]

Carmi

[11] Patent Number: Plant 9,751

[45] Date of Patent: Dec. 17, 1996

[54] HYBRID TEA ROSE PLANT NAMED 'CARSOOF'

[75] Inventor: Carmel Carmi, Moshav Hayogev, Israel

[73] Assignee: Yoval Agricultural Products Ltd., Israel

[21] Appl. No.: 351,865

[22] Filed: Oct. 14, 1994

[51] Int. Cl.[6] ..... A01H 5/00

[52] U.S. Cl. ..... Plt./14

[58] Field of Search ..... Plt./11, 15, 14

[56] References Cited

U.S. PATENT DOCUMENTS

P.P. 8,618 3/1994 Evers ..... Plt./17

OTHER PUBLICATIONS

Modern Roses 10., 1993, The American Rose Society, Shreveport, Louisiana, p. 562.

*Primary Examiner*—Howard J. Locker
*Attorney, Agent, or Firm*—Pollock, Vande Sande & Priddy

[57] ABSTRACT

A new and distinct rose plant of the Hybrid Tea class named 'Carsoof'. The plant is characterized by vigorous growth, non-fragrant yellow-white (R.H.S. 158 B) colored flowers, early and prolific flower production, fast and good propagating features, and very good self-rooting characteristics.

3 Drawing Sheets

CROSS REFERENCE TO RELATED PATENTS

The new and distinct cultivar described and illustrated herein is to related the cultivar 'Saphir', also know as Tanrikas, of Rosen Tanatu, Matias Tantau Nachfolger. Tanrikas is the subject of U.S. Plant Pat. No. 8,618 to Evers.

FIELD OF THE INVENTION

The present invention is concerned with a new variety of a Hybrid Tea rose discovered by me and being a mutation of 'Saphir'.

BACKGROUND OF THE INVENTION

This mutation was discovered as a branch of on a 'Saphir' plant in 1993 on a cultivated area in a farm, located in Moshav Ha'yogev, located in Izra'el Valley, Israel with an average night temperature of 25° C. in summer and 0°–5° C. in winter.

The branch was vegetatively propagated from cuttings by self-rooting. From these cuttings plants were grown in a green house where they were further vegetatively propagated from cuttings by self-rooting.

The resulting plants were found to be stable in their botanical characteristics, as are described below and as illustrated by typical plants parts in the attached photographs.

Asexual propagative of this new variety was performed at Moshav Ha'yogev, Israel.

The presently claimed cultivar was a natural mutation of the cultivar Saphir. The data in the following table of comparison is based on observations made in the greenhouse at Moshav Ha'yogev, where plants were grown side-by-side, under the same conditions and under the same roof. The following observations were made between the present invention and the parent plant.

| | CARSOOF | SAPHIR (TANRIKAS) |
|---|---|---|
| hue of anthocyanin coloration | red-brown | red-green |
| Leaf: | | |
| size: | | |
| length | 100–145 mm | 100–150 mm |
| width | 90–130 mm | 85–135 mm |
| glossiness of upper side | medium | strong |
| Patiole: | | |
| rachis | dark green, rough | green, smooth under side |
| Foliage: | | |
| mature: color: (upper side): | dark green | dark green, very glossy |
| quantity | medium | abundant |
| Flower bud: | | |
| longitudinal section | ovoid | round |
| Flower: | | |
| number of petals | 21–30 | 18–29 |
| side view (upper side): | convex to flattened | concave |
| fragrance | none | slight |
| color fading with age | none | slight fading begins after 3 days |
| life: | | |
| on the plant | 20 days | 16–18 days |
| in a vase | 12–14 days | 10–12 days |
| Sepal: | | |
| extensions | few | very few to few |
| Petal: | | |
| size: | | |
| length | 40–50 mm | 39–45 mm |
| width | 38–50 mm | 37–43 mm |
| shape | rounded with slight tendency to pointed at tip | round |
| upper side: | | |
| color | RHS 158B (whiter than yellow white) | RHS 38A (salmon pink) |

-continued

| | CARSOOF | SAPHIR (TANRIKAS) |
|---|---|---|
| basal spot | none | present |
| lower side: | | |
| color | RHS 158B (whiter than yellow white) | RHS 38 A (salmon pink) |
| basal spot | none | present |
| Guard petal: | generally very light pink | occasional green streak |
| Stamen: | | |
| predominant color of filament | white | pink-white |
| Style: | | |
| color | light green | reddish |
| Anthers: | | |
| color | white | yellow |
| length | short | medium |
| Filament: | | |
| color | yellow-orange | reddish |

All color definitions in this application are taken from The Royal Horticultural Society of Longon, England, (R.H.S.) Color Chart.

SUMMARY OF THE INVENTION

The present invention provides a Hybrid Tea rose variety which includes the following characteristics which distinguish the new variety from the cultivar to which it is related:

Distinctly different in the following:

Young shoot: Hue of anthocyanin coloration.
Leaf: Length, width, glossiness of upper half.
Petiole: Rachis.
Foliage: Color, quantity.
Flower bud: Longitudinal section.
Flower: Average number of petals, side view of upper side, fragrance, color, fading with age, life both on the plant and in a vase.
Sepal: Extensions.
Petal: Size, shape, color, basal spot.
Guard petals: Color.
Stamen: Predominant color of filament.
Style: Color.
Anthers: Color, size.
Filament: Color.

BRIEF DESCRIPTION OF THE DRAWINGS

Sheet 1 represents a typical specimen of the present invention, illustrating a flower bud at picking stage, a petal, a part of the stem, leaflets, and flowers ar various opening stages;

Sheet 2 represents a side-by-side comparison of the flower size, bud size and color of petal between a typical specimen of the present invention, 'Carsoof' (on the left), and the parent variety, 'Saphir' (on the right); and Sheet 3 represents a typical specimen of typical petals and other parts of a flower of the present invention.

The colors in the drawings are as true as reasonably possible in an illustration, depicting green and red colors. The photographs were taken from comparable specimens, grown under exactly the same conditions, in a greenhouse at Moshav Ha'yogev, each on its own roots, and being visibly healthy.

BOTANICAL DESCRIPTION

The following observations were made in Moshav Ha'yogev, Israel, in 1993 in a greenhouse.

Plant:
*Form.*—Bush.
*Growth habit.*—Semi-upright.
*Height (cm).*—150–200.
*Spread (cm).*—Ca. 50.
Wood:
*Color.*—Young: Light green. Mature: Light green.
*Bark color.*—Young: Light green. Mature: Green/corky.
Stem:
*Color.*—Young: R.H.S. 144 A/152 A yellow. Mature: R.H.S. 143 A green.
Young shoot:
*Anthocyanin coloration.*—Medium to strong.
*Hue of anthocyanin.*—Red-brown.
Prickle(s): Present.
*Size.*—Length (mm): Ca 7.5.
*Height (mm).*—Ca 4.5.
*Shape.*—Upper side: Flattened. Lower side: Concave.
*Color.*—Young: Green yellow. Mature: Light brown.
Short prickles:
*Quantity per 10 cm at center of stem.*—Very few (3).
Long prickles:
*Quantity per 10 cm at center of stem.*—Few (6).
Leaf:
*Size.*—Length (mm): 100–145. Width (mm): 90–130.
*Green color.*—Dark.
*Glossiness of upper side.*—Medium.
*Number of leaflets in the compound leaf.*—3, 5, or 7.
Leaflet:
*Cross section.*—Straight.
*Undulation of margin.*—Weak to medium.
*Margin.*—Serrated.
Terminal leaflet:
*Length of blade (mm).*—65–90.
*Maximum width (mm).*—15–25.
*Shape.*—Base: Rounded.
*Description.*—Smooth shiny.
Petiole:
*Length (mm).*—15–22.
*Color.*—R.H.S. 144 A yellow green.
*Rachis.*—Dark green, rough.
Foliage:
*Young.*—Color: Upper side: R.H.S. 152 A yellow green. Lower side: R.H.S. 176 A grey orange.
*Mature.*—Color: Upper side: R.H.S. 137 A green. Lower side: R.H.S. 138 A green.
*Quantity.*—Medium.
Thorns:
*Color.*—Young: R.H.S. 173 A grey orange. Mature: R.H.S. 199 A grey brown.
Stipule: Short, hairy.
Bloom:
*Borne.*—Multiply/in a cluster.
Flowering shoot:
*Number of flowers.*—Few (7).
Flowering habit: Continuous.
Flowering stem:
*Length (cm).*—Long (ca. 60).
*Color.*—Green.
Flower pedicel:
*Number of hairs or prickles.*—Few.
Flower bud:
*Longitudinal section.*—Ovoid.

Flower:
*Type.*—Double.
*Diameter (mm).*—Ca. 85.
*Fragrance.*—None.
*View from above.*—Rounded.
*Side view.*—Upper side: Convex to flattened. Lower side: Flattened.
*Number of petals.*—21–30.
*Life.*—On the plant: Very long: 20 days. In a vase: Very long: 12–14 days.
*Fading with age.*—Stable (none).
Sepal:
*Length (mm).*—35–50.
*Extensions.*—Very weak to weak.
*Color.*—Upper side: R.H.S. 144 B/D yellow green. Lower side: R.H.S. 144 A yellow green.
Petal:
*Size.*—Length (mm): 39–50. Width (mm): 38–50.
*Shape.*—Rounded with slight tendency to pointed at tip.
*Upper side.*—Color: Middle zone: R.H.S. 158 B (whiter than yellow-white). Marginal zone: R.H.S. 158 B (whiter then yellow-white). Basal spot: None.
*Lower side.*—Color: Middle zone: R.H.S. 158 B (whiter than yellow-white). Marginal zone: R.H.S. 158 B (whiter than yellow-white). Basal spot: None.
*Reflexing of margin.*—Medium.
*Undulation of margin.*—Medium.
Stamen:
*Predominant color of filament.*—White.
Style:
*Length.*—Long.
*Predominant color.*—White — light purple.
*Hairiness of upper half.*—Medium.
*Color.*—Light green.
Stigma:
*Position as compared with anthers.*—Same level.
*Color.*—Light green.
Seed vessel:
*Size.*—Small.
*Length (mm).*—8.
*Diameter (mm).*—11.5.
*Shape of longitudinal section.*—Funnel shaped.
*Color.*—Green.
*Description.*—Hairy.
Pollen: Yellow.
Anthers:
*Color.*—White.
*Quantity.*—Many.
*Arrangement.*—Peripheral.
Filament:
*Color.*—Yellow-orange.
*Description.*—Folded triangle.
Time from planting to beginning of flowering: Early: 3 months.
Self-rooting: Very good.

The cultivar is intended as and is suitable as a greenhouse rose. The cultivar bears blooms multiply. Blooms may be borne in a cluster.

When reference is made herein to "Number of flowers few," it is understood that such refers to 3, 4 or 5 flowers per cluster. In addition, the term "fast" represents: within one month from insertion (of the cutting into the bedding) to a commercial plant. The term "good" represents about 60–70% success in propagation.

I claim:

1. A new and distinct rose plant of the Hybrid Tea class named 'Carsoof' as shown and described; said plant being characterized by vigorous growth, non-fragrant yellow-white (R.H.S 158 B) colored flowers, early and prolific flower production, fast and good propagating features, and very good self-rooting characteristics.

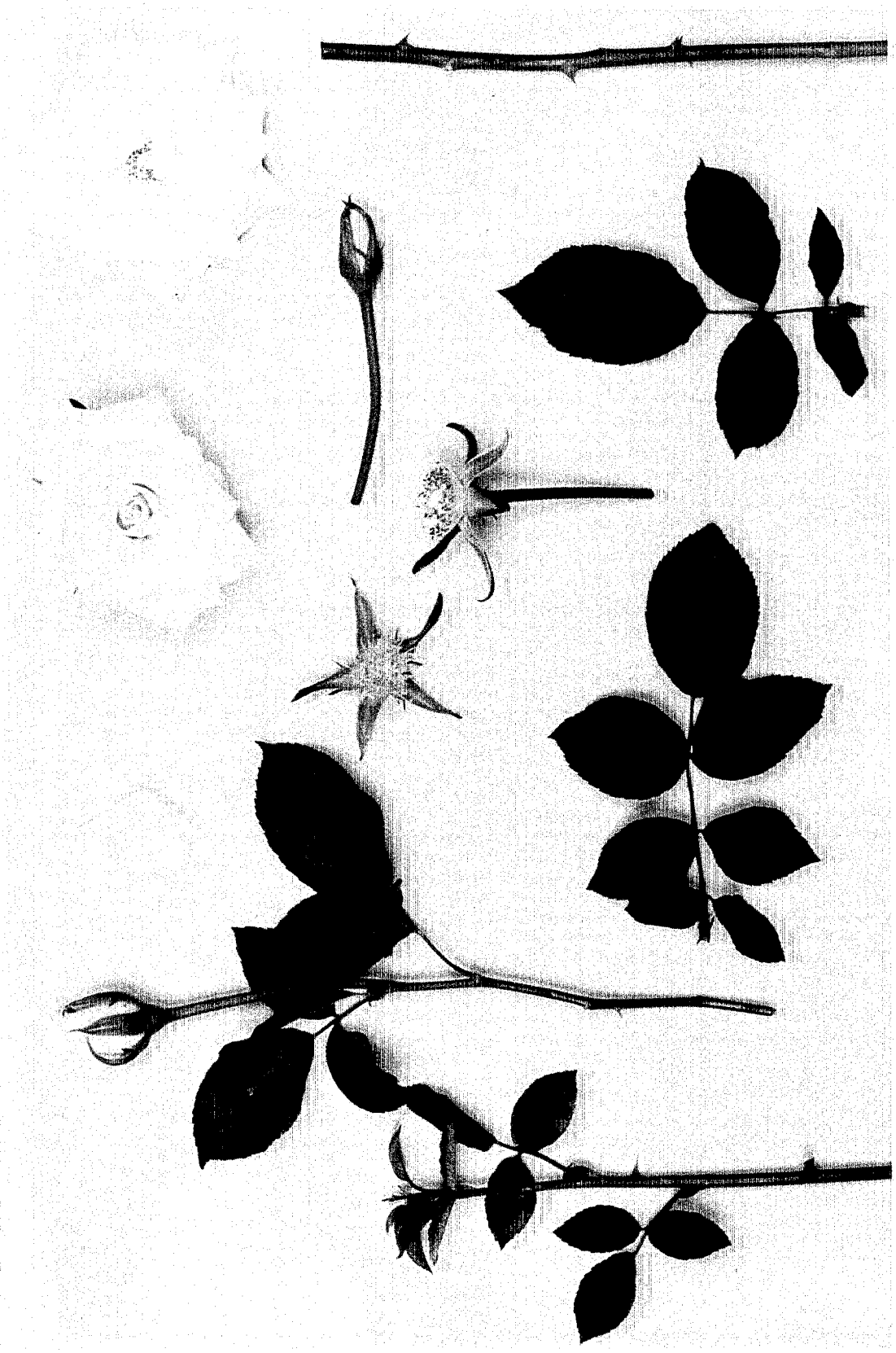

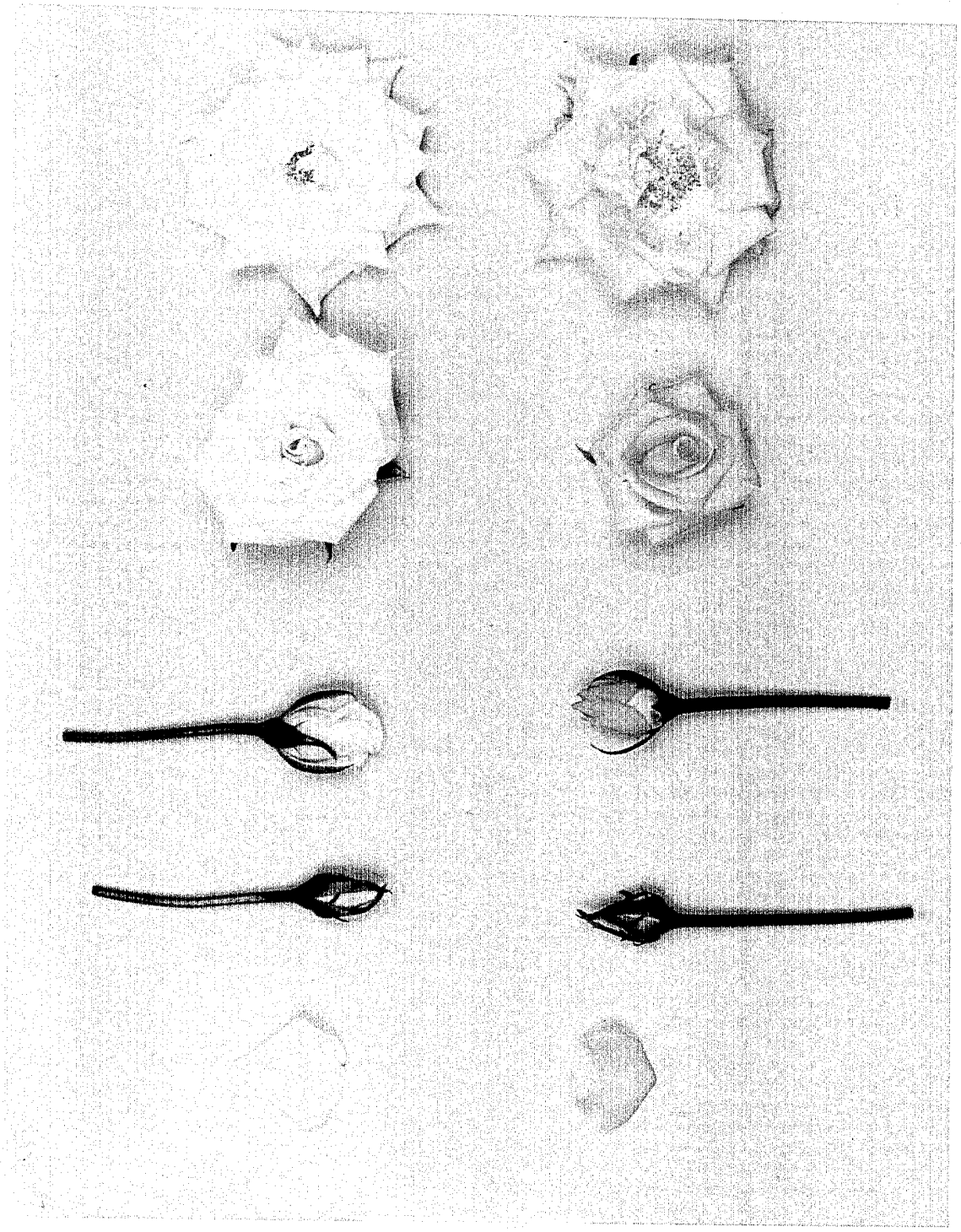

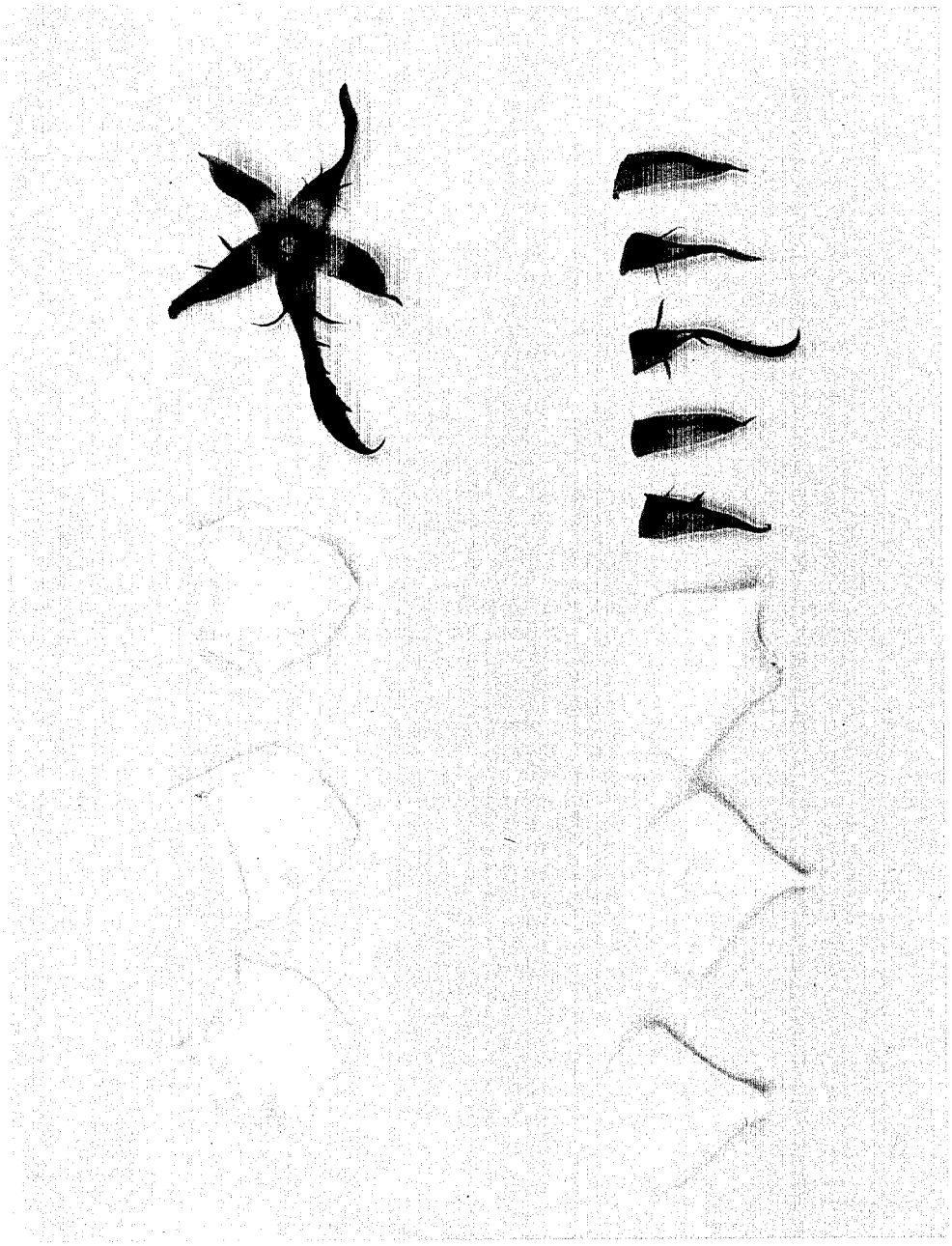

* * * * *